United States Patent
Grosman et al.

(10) Patent No.: US 10,001,450 B2
(45) Date of Patent: Jun. 19, 2018

(54) NONLINEAR MAPPING TECHNIQUE FOR A PHYSIOLOGICAL CHARACTERISTIC SENSOR

(71) Applicant: MEDTRONIC MINIMED, INC., Northridge, CA (US)

(72) Inventors: Benyamin Grosman, North Hollywood, CA (US); Desmond Barry Keenan, Hollywood, CA (US); John J. Mastrototaro, Los Angeles, CA (US); Rajiv Shah, Rancho Palos Verdes, CA (US); Andrea Varsavsky, Santa Monica, CA (US); Ning Yang, Los Angeles, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1021 days.

(21) Appl. No.: 14/256,229

(22) Filed: Apr. 18, 2014

(65) Prior Publication Data
US 2015/0300969 A1    Oct. 22, 2015

(51) Int. Cl.
*C25D 3/38* (2006.01)
*G01N 27/02* (2006.01)

(52) U.S. Cl.
CPC ................................ *G01N 27/026* (2013.01)

(58) Field of Classification Search
None
See application file for complete search history.

(56) References Cited

U.S. PATENT DOCUMENTS

| 3,631,847 | A | 1/1972 | Hobbs, II |
| 4,212,738 | A | 7/1980 | Henne |
| 4,270,532 | A | 6/1981 | Franetzki et al. |
| 4,282,872 | A | 8/1981 | Franetzki et al. |
| 4,373,527 | A | 2/1983 | Fischell |

(Continued)

FOREIGN PATENT DOCUMENTS

| DE | 4329229 | 3/1995 |
| EP | 0319268 | 11/1988 |

(Continued)

OTHER PUBLICATIONS (Animas Corporation, 1999). Animas . . . bringing new life to insulin therapy.

(Continued)

*Primary Examiner* — Jill A Warden
*Assistant Examiner* — Brittany I Fisher
(74) *Attorney, Agent, or Firm* — Lorenz & Kopf, LLP

(57) ABSTRACT

A method of measuring blood glucose of a patient is presented here. In accordance with certain embodiments, the method applies a constant voltage potential to a glucose sensor and obtains a constant potential sensor current from the glucose sensor, wherein the constant potential sensor current is generated in response to applying the constant voltage potential to the glucose sensor. The method continues by performing an electrochemical impedance spectroscopy (EIS) procedure for the glucose sensor to obtain EIS output measurements. The method also performs a nonlinear mapping operation on the constant potential sensor current and the EIS output measurements to generate a blood glucose value.

20 Claims, 4 Drawing Sheets

(56) References Cited

U.S. PATENT DOCUMENTS

| | | |
|---|---|---|
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A * | 12/1999 | Gord .................... H02M 7/219 327/104 |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |

(56) References Cited

U.S. PATENT DOCUMENTS

| | | |
|---|---|---|
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 9,510,782 B2 * | 12/2016 | Kamath ............ A61B 5/14532 |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0240540 A1 * | 10/2006 | Nakatsuka ......... G01N 27/3272 435/287.2 |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0033254 A1 * | 2/2008 | Kamath ............ A61B 5/14532 600/300 |
| 2008/0154503 A1 | 6/2008 | Wittenber et al. |
| 2008/0262387 A1 * | 10/2008 | List ................. A61B 5/150022 600/583 |
| 2009/0081951 A1 | 3/2009 | Erdmann et al. |
| 2009/0082635 A1 | 3/2009 | Baldus et al. |
| 2012/0108933 A1 * | 5/2012 | Liang ................... A61B 5/0002 600/365 |
| 2012/0262298 A1 * | 10/2012 | Bohm ................ G01N 27/3274 340/604 |
| 2013/0060105 A1 * | 3/2013 | Shah .................... A61B 5/6849 600/316 |
| 2013/0183243 A1 * | 7/2013 | LaBelle ............. G01N 33/5438 424/9.1 |
| 2013/0328573 A1 * | 12/2013 | Yang .................... G01R 35/00 324/601 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | PCT/US02/03299 | 10/2002 |
| WO | WO 03/001329 | 1/2003 |
| WO | WO 03/094090 | 11/2003 |
| WO | WO 2005/065538 A2 | 7/2005 |
| WO | WO2013/184416 A2 | 12/2013 |

OTHER PUBLICATIONS

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation in the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

(56) References Cited

OTHER PUBLICATIONS

Walsh J, et al. (1989). Pumping Insulin: The Art of Using an Insulin Pump. Published by MiniMed•Technologies.
(Intensive Diabetes Management, 1995). Insulin Infusion Pump Therapy. Pages 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump For those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytics Chimica Acta, 249, 1991, pp. 43-54.

Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a minia-

(56) References Cited

OTHER PUBLICATIONS turized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes VVho Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: a useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pgs. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

NONLINEAR MAPPING TECHNIQUE FOR A PHYSIOLOGICAL CHARACTERISTIC SENSOR

TECHNICAL FIELD

Embodiments of the subject matter described herein relate generally to physiological characteristic sensors, such as glucose sensors. More particularly, embodiments of the subject matter relate to a calibration free blood glucose sensor that utilizes nonlinear mapping techniques.

BACKGROUND

The prior art is replete with sensors, systems, and medical devices that are designed to measure, process, monitor, and/or display physiological characteristics of a patient. For example, the prior art includes glucose sensor devices and systems that monitor blood glucose levels in a subject's body on a continuing basis. Presently, a patient can measure his/her blood glucose (BG) using a BG measurement device, which may be: a glucose meter such as a test strip meter; a continuous glucose measurement system or monitor; a hospital hemacue; or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement can be output, displayed, processed, or otherwise handled in an appropriate manner.

Currently known continuous glucose measurement systems include subcutaneous (or short-term) sensors and implantable (or long-term) sensors. The current state of the art in continuous glucose monitoring (CGM) is largely adjunctive, meaning that the readings provided by a CGM device (including, e.g., an implantable or subcutaneous sensor) cannot be used without a reference value in order to make a clinical decision. The reference value, in turn, must be obtained from a blood sample, which may be obtained from a BG meter (such as a finger stick device). The reference value can be used to check the accuracy of the sensor, and it can also be used to generate a calibration factor that is applied to the raw sensor data.

The art has searched for ways to eliminate or, at the very least, minimize, the number of finger stick measurements that are necessary for calibration and for assessing sensor health. However, given the number and level of complexity of the multitude of sensor operating modes, no satisfactory solution has been found. At most, diagnostics have been developed that are based on either direct assessment of the sensor output current (Isig), or on comparison of two Isig values. In either case, because the Isig tracks the level of glucose in the body, by definition, it is not analyte independent. As such, by itself, the Isig is not a reliable source of information for sensor diagnostics, nor is it a reliable predictor for continued sensor performance.

Accordingly, it is desirable to have an improved physiological characteristic sensor and related sensor system that addresses the shortcomings of traditional sensor systems. In addition, it is desirable to have a calibration free BG sensor that need not rely on BG finger stick samples. Furthermore, other desirable features and characteristics will become apparent from the subsequent detailed description and the appended claims, taken in conjunction with the accompanying drawings and the foregoing technical field and background.

BRIEF SUMMARY

A method of measuring blood glucose of a patient is provided here. The method applies a constant voltage potential to a glucose sensor and obtains a constant potential sensor current from the glucose sensor. The constant potential sensor current is generated in response to applying the constant voltage potential to the glucose sensor. The method continues by performing an electrochemical impedance spectroscopy (EIS) procedure for the glucose sensor to obtain EIS output measurements, and by performing a nonlinear mapping operation on the constant potential sensor current and the EIS output measurements to generate a blood glucose value.

An exemplary embodiment of a sensor system is also presented here. The sensor system includes a sensor electrode and sensor electronics coupled to the sensor electrode. The sensor electronics apply a constant voltage potential to the sensor electrode, and obtain a constant potential sensor current from the sensor electrode, wherein the constant potential sensor current is generated in response to applying the constant voltage potential to the sensor electrode. The sensor electronics also perform an EIS procedure for the sensor electrode to obtain EIS output measurements, and perform a nonlinear mapping operation on the constant potential sensor current and the EIS output measurements to generate a sensor output value.

Also provided is an exemplary embodiment of a sensor system having a processor-readable storage medium having executable instructions stored thereon. The executable instructions implement a method that obtains a constant potential sensor current from a glucose sensor, wherein the constant potential sensor current is obtained in response to application of a constant voltage potential to the glucose sensor. The method continues by obtaining EIS output measurements from the glucose sensor, wherein the EIS output measurements are obtained in response to application of alternating current (AC) voltage signals to the glucose sensor. The method also performs a nonlinear mapping operation on the constant potential sensor current and the EIS output measurements to generate a blood glucose value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components, processing logic, or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

Figure 1:
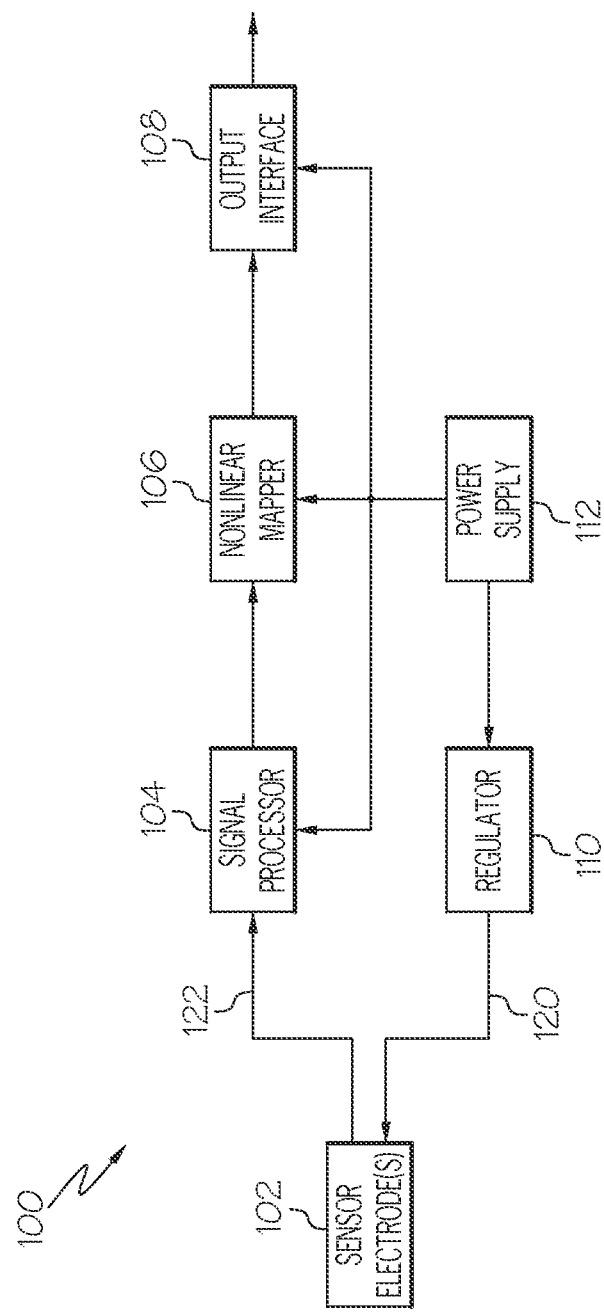
FIG. 1 is a schematic representation of a physiological characteristic sensor system configured in accordance with an exemplary embodiment.

FIG. 1 is a schematic representation of a physiological characteristic sensor system 100 configured in accordance with an exemplary embodiment. The sensor system 100 is suitably configured to measure a physiological characteristic of the subject, e.g., a human patient. In accordance with the non-limiting embodiments presented here, the physiological characteristic of interest is blood glucose, and the sensor system 100 generates output that is indicative of a blood glucose level of the subject. It should be appreciated that the techniques and methodologies described here may also be utilized with other sensor types if so desired.

FIG. 1 depicts a simplified representation of the sensor system 100; in practice the sensor system 100 may include additional elements and functionality that are unrelated or unimportant to the subject matter presented here. Moreover, the sensor system 100 may incorporate or utilize any of the relevant subject matter that is disclosed in the PCT patent application titled APPLICATION OF ELECTROCHEMICAL IMPEDANCE SPECTROSCOPY IN SENSOR SYSTEMS, DEVICES, AND RELATED METHODS, published Dec. 12, 2013 as International Publication Number WO 2013/184416 A2 (the content of which is incorporated by reference herein).

The illustrated embodiment of the sensor system 100 generally includes, without limitation: at least one sensor electrode 102; a signal processor 104; a nonlinear mapper 106; an output interface 108; a regulator 110; and a power supply 112. The elements of the sensor system 100 are coupled together or are otherwise designed to cooperate as needed to support the techniques, methodologies, and operation described in more detail herein. Some or all of the blocks shown in FIG. 1 (e.g., the signal processor 104, the nonlinear mapper 106, and the regulator 110) may include, cooperate with, or be implemented as software, firmware, and/or processing logic. To this end, the sensor system 100 may include one or more processors and one or more processor-readable storage media having executable instructions stored thereon. The executable instructions, when executed by a processor, are capable of implementing the various methods, processes, and techniques described in more detail below. For example, the nonlinear mapper 106 may be realized using suitably written instructions that perform the desired mapping functions.

The elements depicted in FIG. 1 can be implemented and realized in a variety of different ways, depending on the desired application, device platform, and operating environment. For example, all of blocks illustrated in FIG. 1 could be integrated into a single device or component, such as a glucose sensor device that communicates with a monitor device, an insulin pump device, or a computer. As another example, some of the illustrated blocks (such as the signal processor 104, the nonlinear mapper 106, and the output interface 108) could be implemented in a physically distinct device that communicates with a glucose sensor device that houses the sensor electrodes 102, the regulator, and the power supply 112. These and other implementation and deployment options are contemplated by this disclosure.

The sensor electrodes 102 are designed for subcutaneous placement at a selected site in the body of a user. When placed in this manner, the sensor electrodes 102 are exposed to the user's bodily fluids such that they can react in a detectable manner to the physiological characteristic of interest, e.g., blood glucose level. In certain embodiments, the sensor electrodes 102 may include a counter electrode, a reference electrode, and one or more working electrodes. For the embodiments described here, the sensor electrodes 102 employ thin film electrochemical sensor technology of the type used for monitoring blood glucose levels in the body. Further description of flexible thin film sensors of this general type are found in U.S. Pat. No. 5,391,250, entitled METHOD OF FABRICATING THIN FILM SENSORS, which is herein incorporated by reference. In other embodiments, different types of implantable sensor technology, such as chemical based, optical based, or the like, may be used.

The sensor electrodes 102 cooperate with sensor electronics, which may be integrated with the sensor electrodes 102 in a sensor device package, or which may be implemented in a physically distinct device or component that communicates with the sensor electrodes 102 (such as a monitor device, an infusion pump device, a controller device, or the like). In this regard, any or all of the remaining elements shown in FIG. 1 may be included in the sensor electronics, as needed to support the particular embodiment.

For purposes of this example, the sensor electronics include the signal processor 104, the nonlinear mapper 106, the output interface 108, the regulator 110, and the power supply 112. The power supply 112 provides power (in the form of either a voltage, a current, or a voltage including a current) to the regulator 110. The power supply 112 may also be suitably configured to provide operating power to the signal processor 104, the nonlinear mapper 106, and/or the output interface 108 as needed. In certain embodiments, the power supply 112 is realized using one or more batteries.

The regulator 110 generates and applies regulated voltage to the sensor electrodes 102. In certain embodiments, the regulator 110 applies voltage to the counter electrode of the sensor electrodes 102. As described in more detail below, the regulator 110 generates and applies DC voltage to the sensor electrodes 102 during a first excitation mode to obtain a constant potential sensor current (Isig) that is indicative of the blood glucose level. In addition, the regulator 110 generates and applies AC voltage (at different frequencies) to the sensor electrodes 102 during an electrochemical impedance spectroscopy (EIS) excitation mode to carry out an EIS procedure during which EIS output measurements are obtained from the sensor electrodes 102. Thus, the regulator 110 is responsible for managing the excitation voltage characteristics, frequencies, magnitudes, and timing required to support the sensor operating methodologies described herein.

When driven by an excitation voltage signal 120, the sensor electrodes 102 respond in a way that is indicative of a concentration of a physiological characteristic being measured. For this example, the sensor output signal 122 may be indicative of a blood glucose reading. In certain embodiments, the sensor output signal 122 is present at the working electrode of the sensor electrodes 102. In practice, the sensor output signal 122 may be a current or a voltage measured at the working electrode. During an EIS procedure, the sensor output signal 122 is indicative of an impedance at the given frequency, an amplitude, and a phase angle.

The signal processor 104 receives the sensor output signals 122 that are produced in response to the application of corresponding DC or AC voltage to the sensor electrodes 102. The signal processor 104 processes the sensor output signals 122 and generates processed sensor signals that are suitable for use as inputs to the nonlinear mapper 106. The nonlinear mapper 106 receives the processed sensor signals and performs a nonlinear mapping operation to generate a corresponding blood glucose value. The nonlinear mapper 106 utilizes a sensor characterization model for the particular type of sensor, wherein the model generates the blood glucose value in the absence of any calibration factor or linear translation. In this regard, the nonlinear mapper 106 is designed and programmed in a way that accurately generates blood glucose values in a calibration-free manner that does not require BG meter (finger stick) measurements. Moreover, the nonlinear mapper 106 is designed and programmed such that the output mapping automatically compensates for typical manufacturing tolerances, shelf life, operating age, and other changes to the sensor system 100 that would normally be corrected by way of frequent calibration routines.

The BG values generated by the nonlinear mapper 106 may be provided to the output interface 108, which in turn may generate an appropriate output that conveys the BG values. For example, the output interface 108 may include or cooperate with a display driver and graphics processor to render the BG values on a display element (not shown). As another example, the output interface 108 may include or cooperate with a data communication module, such as a network interface, a wireless transmitter, a modem, or the like. The output interface 108 can be designed to support any output format or methodology as appropriate to the particular embodiment. In this regard, the output interface 108 may communicate with any or all of the following, without limitation: a display device; a computer; a pager; a television set; a server; a mobile telephone device; an infusion pump including a display; a personal medical device; hospital equipment; or the like.

Figure 2:
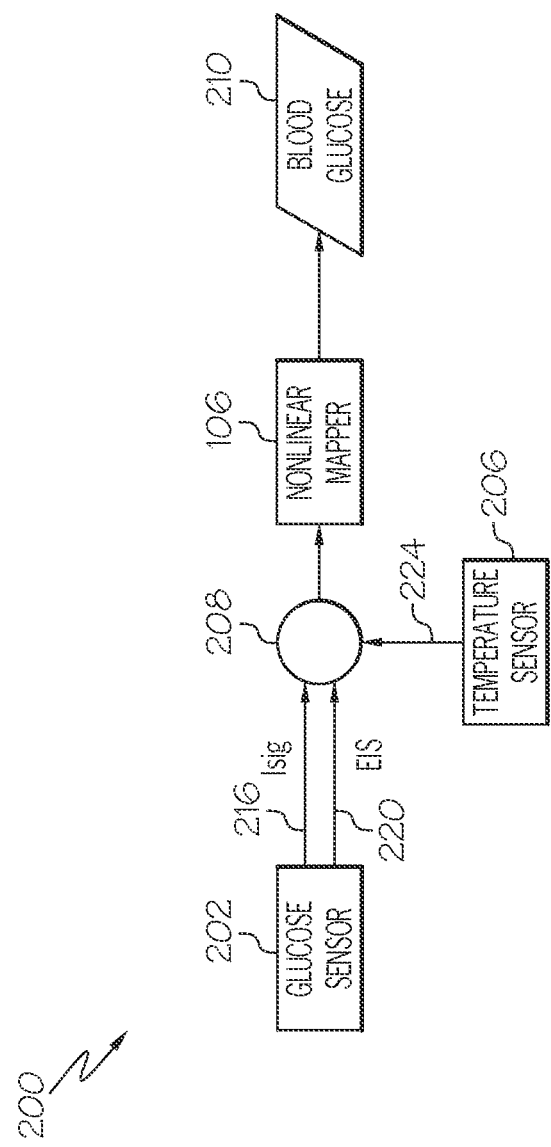
FIG. 2 is a schematic representation of a BG sensor system according to an exemplary embodiment.

FIG. 2 is a schematic representation of a BG sensor system 200 according to an exemplary embodiment. The system 200 depicted in FIG. 2 may correspond to the sensor system 100 depicted in FIG. 1 (but illustrated in a different manner). FIG. 2 focuses more on the nonlinear mapping functionality of the system 200. Accordingly, conventional elements that are unimportant or unrelated to the nonlinear mapping feature are not shown in FIG. 2. For this particular embodiment, the BG sensor system 200 includes, without limitation: a glucose sensor 202; the nonlinear mapper 106; a temperature sensor 206; and a mixer or combiner element 208. These elements cooperate to generate output data that is indicative of a BG value 210 for the monitored subject.

The glucose sensor 202 may include or cooperate with sensor electrodes, a power supply, a regulator, a signal processor, and/or other features or components as described above with reference to FIG. 1. The glucose sensor 202 is preferably realized as an electrochemical component that reacts to glucose levels within the body of the subject. As is well known to those familiar with glucose sensor technology, the glucose sensor 202 may employ a glucose oxidase (GOx) enzyme for catalyzing a reaction with the sensor electrodes. The reaction is responsive to electrical stimulation of the glucose sensor 202, and characteristics of the output signals of the glucose sensor 202 are indicative of the current BG level.

The glucose sensor 202 can be operated in at least two stimulation modes: a DC stimulation mode during which a constant voltage potential is applied to the glucose sensor 202; and an AC stimulation mode during which an alternating current voltage signal is applied to the glucose sensor 202. In some embodiments, the DC stimulation mode and the AC stimulation mode are active at different times. In other embodiments, the DC stimulation mode and the AC stimulation mode occur concurrently. Moreover, the DC stimulation mode may have a different timing scheme relative to the AC stimulation mode. For example, the glucose sensor 202 may be operated in the DC stimulation mode once every five minutes, and operated in the AC stimulation mode once every thirty minutes. Furthermore, the duration of the DC stimulation mode need not be the same as the duration of the AC stimulation mode. In certain embodiments, the AC stimulation mode requires more time than the DC stimulation mode because AC signals having a plurality of different frequencies are applied to the glucose sensor 202 during the AC stimulation mode.

The glucose sensor 202 reacts to a DC voltage in a way that is influenced by the BG level in the body of the subject. The resulting constant potential sensor current (referred to herein as "Isig") serves as the raw sensor output during the DC stimulation mode. Thus, Isig varies in accordance with changes to the BG level of the subject. As depicted in FIG. 2, the Isig values may serve as one input to the combiner element 208. In accordance with many traditional glucose measurement approaches, Isig values are subjected to a linear calibration factor (which must be updated frequently during the life of the glucose sensor) to obtain an estimated BG value that accurately tracks the subject's actual blood glucose level. In contrast, the raw Isig values 216 obtained from the glucose sensor 202 need not be adjusted by any calibration factor.

As mentioned above, the glucose sensor 202 is also operated in an AC stimulation mode to obtain additional output measurements. The AC stimulation mode corresponds to an electrochemical impedance spectroscopy (EIS) procedure, which is performed for the glucose sensor 202. The glucose sensor 202 responds to the EIS procedure such that EIS output measurements 220 can be obtained. The EIS procedure is performed independently of the DC stimulation mode in that the AC voltage signals associated with the EIS procedure are applied to the glucose sensor 202 at different times than the DC voltage signals. Moreover, the timing associated with the application of the DC voltage signals and the AC voltage signals may vary. For example, the DC stimulation mode may be performed once every five minutes, while the AC stimulation mode may be performed once every thirty minutes.

For this particular embodiment, the EIS procedure is performed for a plurality of different frequencies. Accordingly, the glucose sensor 202 responds to each AC voltage signal such that a respective set of EIS output measurements 220 are obtained. The EIS output measurements 220 for all of the different AC frequencies can be collected and used as additional inputs to the combiner element 208 (as schematically depicted in FIG. 2).

EIS techniques and technology in the context of blood glucose measurement are described in more detail in the PCT patent application published as International Publication Number WO 2013/184416 A2 (the content of which is incorporated by reference herein). In this regard, EIS provides information in the form of sensor impedance and impedance-related parameters at different frequencies. Moreover, for certain ranges of frequencies, impedance and/or impedance-related data are substantially glucose independent. Such glucose independence enables the use of a variety of EIS-based markers or indicators for not only producing a robust, highly-reliable sensor glucose value (through fusion methodologies), but also assessing the condition, health, age, and efficiency of individual electrode(s) and of the overall sensor substantially independently of the glucose-dependent Isig.

EIS, or AC impedance methods, study the system response to the application of a periodic small amplitude AC signal. As is known, impedance may be defined in terms of its magnitude and phase, where the magnitude (|Z|) is the ratio of the voltage difference amplitude to the current amplitude, and the phase (θ) is the phase shift by which the current is ahead of the voltage. When a circuit is driven solely with direct current (DC), the impedance is the same as the resistance, i.e., resistance is a special case of impedance with zero phase angle. However, as a complex quantity, impedance may also be represented by its real and imaginary parts. In this regard, the real and imaginary impedance can be derived from the impedance magnitude and phase.

In performing the EIS procedure and analysis, an AC voltage of various frequencies and a DC bias may be applied between, e.g., the working and reference electrodes of the glucose sensor 202. Although, generally, the EIS procedure may be performed at frequencies in the μHz to MHz range, in certain embodiments, a narrower range of frequencies (e.g., between about 0.1 Hz and about 8 kHz) may be sufficient. Thus, AC potentials may be applied that fall within a frequency range of between about 0.1 Hz and about 8 kHz, with a programmable amplitude of up to at least 100 mV, and preferably at about 50 mV.

EIS may be used in sensor systems where the sensor includes a single working electrode, as well those in which the sensor includes multiple (redundant) working electrodes. In some embodiments, EIS provides valuable information regarding the age (or aging) of the glucose sensor 202. Specifically, at different frequencies, the magnitude and the phase angle of the impedance vary. Moreover, a new sensor normally has higher impedance than a used sensor. Thus, the EIS output measurements can be used to determine information related to the age of the sensor under observation.

The system 200 may also include or cooperate with an optional temperature sensor 206 that provides temperature measurement data 224 as an additional input to the combiner element 208. The temperature measurement data 224 can be used as an additional parameter to generate the blood glucose value 210 with more accuracy. It should be appreciated that the temperature sensor 206 need not be employed, and that the nonlinear mapper 204 can be configured in an appropriate manner to contemplate embodiments that do not use the temperature sensor 206.

The combiner element 208 obtains the Isig values 216, the EIS output measurements 220, and (if available) the temperature measurement data 224 to be used for each calculation of a corresponding BG value 210. The combiner element 208 combines these inputs as needed to accomplish the nonlinear mapping operation (performed by the nonlinear mapper 106). Although FIG. 2 depicts the combiner element 208 as a distinct block, it should be appreciated that the functionality of the combiner element 208 and the nonlinear mapper 106 could be integrated if so desired.

In certain embodiments, each BG value 210 generated by the nonlinear mapper 106 is derived from a combination of at least one Isig value and at least some of the EIS output measurements obtained for an iteration of the EIS procedure. The nonlinear mapper 106, which was described above in the context of FIG. 1, employs a sensor characterization model that accurately produces the BG values 210. The sensor characterization model accurately estimates the subject's actual BG level in a way that compensates for manufacturing variances, age of the glucose sensor 202, and possibly other factors, without requiring any calibrations based on BG meter readings.

Figure 3:
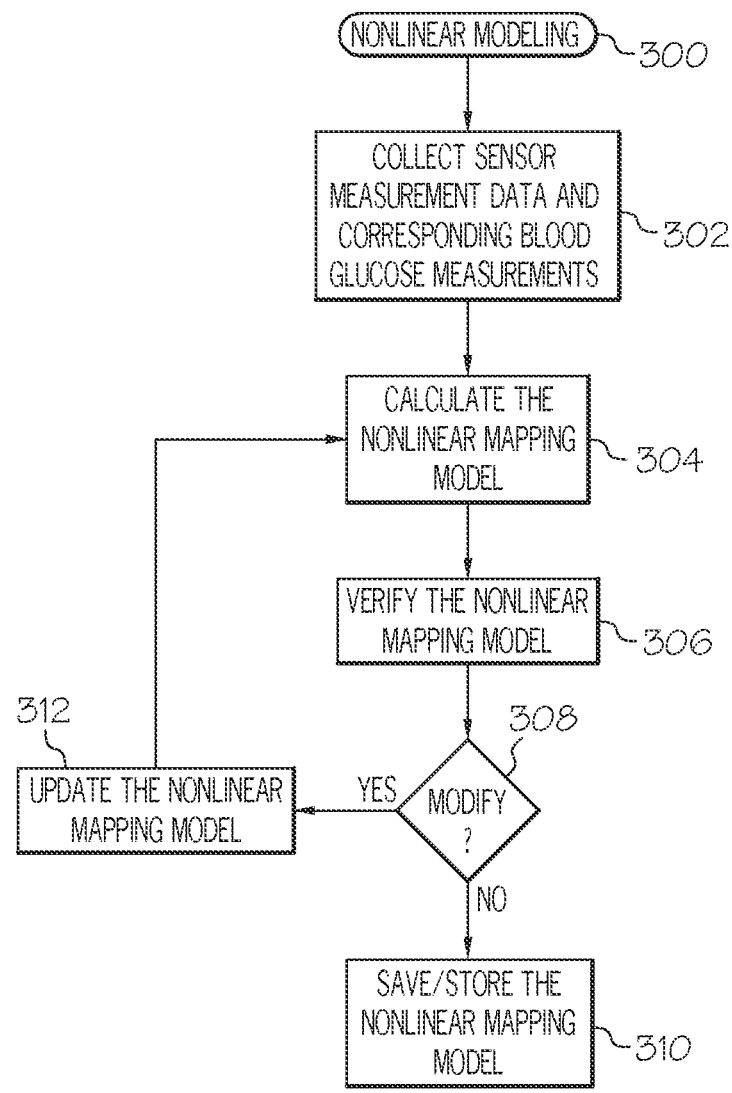
FIG. 3 is a flow chart that illustrates an exemplary embodiment of a nonlinear modeling process.

The sensor characterization model used by the nonlinear mapper 106 can be determined based on empirical measurement data, corresponding BG meter data, and the like. In this regard, FIG. 3 is a flow chart that illustrates an exemplary embodiment of a nonlinear modeling process 300, which may be performed during the design, development, and/or manufacturing of a glucose system of the type described here. The various tasks performed in connection with the process 300 may be performed by software, hardware, firmware, or any combination thereof. For illustrative purposes, the following description of the process 300 may refer to elements mentioned above in connection with FIGS. 1-2. It should be appreciated that the process 300 may include any number of additional or alternative tasks, the tasks shown in FIG. 3 need not be performed in the illustrated order, and the process 300 may be incorporated into a more comprehensive procedure or process having additional functionality not described in detail herein. Moreover, one or more of the tasks shown in FIG. 3 could be omitted from an embodiment of the process 300 as long as the intended overall functionality remains intact.

The process 300 may involve the collection (task 302) of sensor measurement data and corresponding BG measurements (taken, from a finger stick device or other blood sampling device). The collected data may correspond to any number of different sampling/measurement times. The collected data is then analyzed and processed to calculate a corresponding nonlinear mapping model (task 304). Ideally, the model will accurately output the actual measured BG values using the sensor measurement data as the input. In practice, however, the calculated model will be tested or otherwise verified to ensure that the nonlinear mapping algorithm satisfies the desired accuracy metrics (task 306).

If the calculated model is satisfactory and no modifications are needed (the "No" branch of query task 308), then the process 300 saves or stores the nonlinear mapping model in association with the nonlinear mapper (task 310). If, however, the calculated model needs to be modified or refined in some way, then the process 300 updates certain parameters of the nonlinear mapping model in an attempt to improve its accuracy (task 312). Thereafter, a new nonlinear mapping model is calculated (during the next iteration of task 304) and the process 300 continues as described above.

A different nonlinear mapping model can be generated for each sensor type, model, and/or configuration. Ideally, the nonlinear mapping model will consider and contemplate changes to the electrochemical properties and characteristics of the sensor, which may be influenced by the age of the sensor, by manufacturing variations, by the operating conditions or environment, and the like. Thus, the same nonlinear mapping model can be programmed for use in connection with all sensors to be manufactured and sold under the same model number, SKU, etc.

Figure 4:
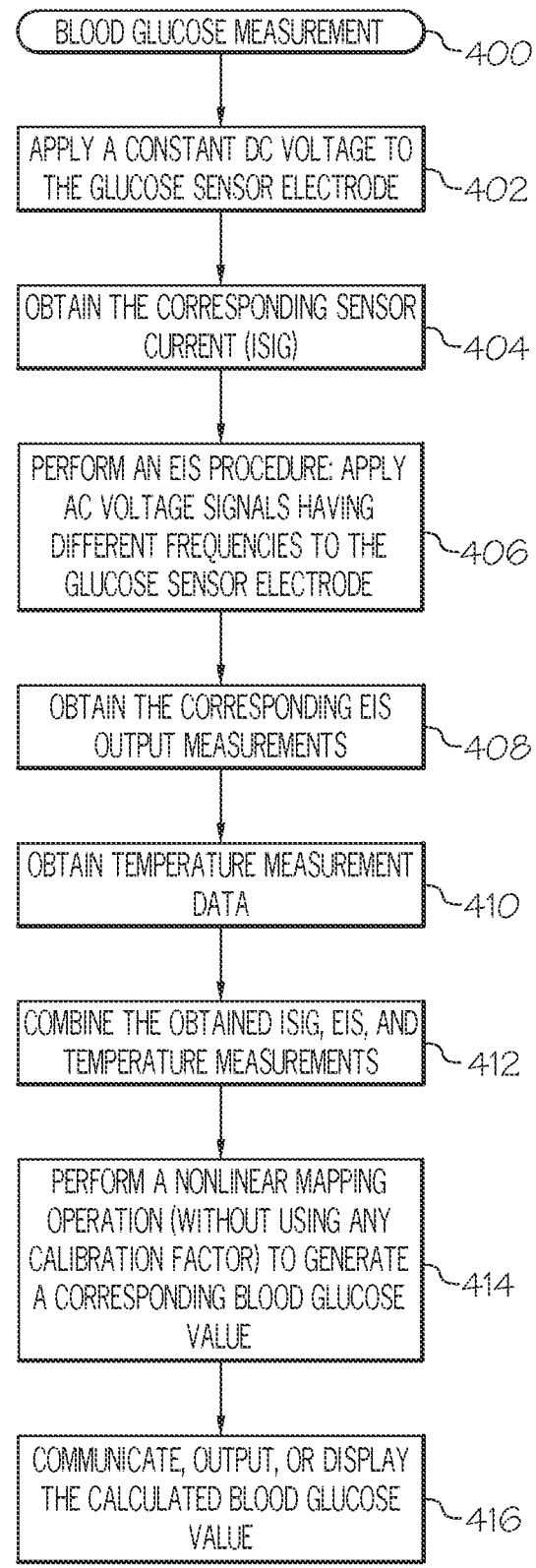
FIG. 4 is a flow chart that illustrates an exemplary embodiment of a BG measurement process.

FIG. 4 is a flow chart that illustrates an exemplary embodiment of a BG measurement process 400, which may be performed by a sensor system of the type described above. The various tasks performed in connection with the process 400 may be performed by software, hardware, firmware, or any combination thereof. For illustrative purposes, the following description of the process 400 may refer to elements mentioned above in connection with FIGS. 1-3. It should be appreciated that the process 400 may include any number of additional or alternative tasks, the tasks shown in FIG. 4 need not be performed in the illustrated order, and the process 400 may be incorporated into a more comprehensive procedure or process having additional functionality not described in detail herein. Moreover, one or more of the tasks shown in FIG. 4 could be omitted from an embodiment of the process 400 as long as the intended overall functionality remains intact.

The measurement process 400 assumes that the nonlinear mapper of the glucose sensor system has been properly trained and configured as described above with reference to the modeling process 300. The process 400 applies a constant DC voltage potential to the glucose sensor (task 402). As explained above, DC voltage is applied to the sensor electrodes during the DC stimulation mode of the glucose sensor. In response to the applied DC voltage, the process 400 obtains the corresponding constant potential sensor current (Isig) from the glucose sensor (task 404).

Thereafter, the glucose sensor is operated in the AC stimulation mode to perform an EIS procedure (task 406). In association with the EIS procedure, AC voltage signals having different frequencies are applied to the glucose sensor. Although the number of different frequencies and the frequency range may vary from one embodiment to another, this non-limiting example utilizes 22 different frequencies. In response to the applied AC voltage signals, the process 400 obtains the corresponding EIS output measurements (task 408) for each of the different frequencies. If available and supported by the particular embodiment, the process 400 also obtains temperature measurement data (task 410) from one or more temperature sensors.

The Isig information, the EIS output measurements, and (if applicable) the temperature measurements can be combined, mixed, conditioned, filtered, or otherwise processed as needed (task 412). Task 412 may be performed to prepare the obtained data for nonlinear mapping. In this regard, the process 400 performs the nonlinear mapping operation (task 414) as defined by the particular sensor characterization model. For this example, nonlinear mapping is performed on the Isig, EIS output measurement, and temperature measurement information associated with the current sampling point or time. Notably, the nonlinear mapping operation is effective at generating a BG value corresponding to the obtained measurement data, in the absence of any linear calibration factors. The calculated BG value produced by the nonlinear mapper can be communicated, output, displayed, saved, or otherwise handled as desired (task 416). The process 400 can be repeated as often as needed to obtain updated BG values in an ongoing manner.

To summarize, nonlinear mapping knowledge is utilized to convert glucose sensor measurement data into accurate BG values. Traditionally, the constant potential electrical signals (Isig) have been mapped in a linear fashion to obtain estimated BG output. In order to overcome divergence in sensor manufacturing, sensor insertion site, patient specific influences, temperature, and many other influences, such conventional glucose sensors need to be calibrated at least once every twelve hours, and a calibration at the beginning of the sensor life is mandatory.

In contrast to traditional approaches, a glucose system of the type described in detail above employs advanced EIS technology that generates frequency dependent impedance electrical signals from the sensor electrode, which in turn can be related to physical quantities or processes such as the membrane resistance or the diffusion characteristics of the materials in the sensor. In addition, the sensor system can potentially collect temperature measurements. This information in addition to the Isig measurements can be nonlinearly mapped into BG values without the need of calibration, and despite the various sensor divergences mentioned previously. The disclosed technology can be implemented to produce a calibration-free continuous glucose sensor that automatically responds to changes in the electrochemical characteristics of the sensor over time.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of measuring blood glucose of a patient, the method comprising:
applying a constant voltage potential to a glucose sensor;
obtaining a constant potential sensor current from the glucose sensor, wherein the constant potential sensor current is generated in response to applying the constant voltage potential to the glucose sensor;

performing an electrochemical impedance spectroscopy (EIS) procedure for the glucose sensor to obtain EIS output measurements; and performing a nonlinear mapping operation on the constant potential sensor current and the EIS output measurements to generate a blood glucose value.

2. The method of claim 1, wherein the nonlinear mapping operation generates the blood glucose value in the absence of any calibration factor for the glucose sensor.

3. The method of claim 1, wherein applying the constant voltage potential and performing the EIS procedure occur at different times.

4. The method of claim 1, wherein performing the EIS procedure comprises:
applying an alternating current (AC) voltage signal to the glucose sensor.

5. The method of claim 1, wherein the EIS procedure is performed for a plurality of frequencies.

6. The method of claim 1, further comprising:
obtaining temperature measurement data, wherein the nonlinear mapping operation is performed on the constant potential sensor current, the EIS output measurements, and the temperature measurement data to generate the blood glucose value.

7. The method of claim 1, wherein the nonlinear mapping operation is associated with a sensor characterization model for the glucose sensor.

8. The method of claim 1, wherein the nonlinear mapping operation comprises:
combining the constant potential sensor current and at least some of the EIS output measurements.

9. A sensor system comprising:
A sensor electrode; and
Sensor electronics coupled to the sensor electrode, the sensor electronics including one or more processors having executable instructions stored thereon, the executable instructions executed by the processor to:
Apply a constant voltage potential to the sensor electrode;
Obtain a constant potential sensor current from the sensor electrode, wherein the constant potential sensor current is generated in response to applying the constant voltage potential to the sensor electrode;
Perform an electrochemical impedance spectroscopy (EIS) procedure for the sensor electrode to obtain EIS output measurements; and
Perform a nonlinear mapping operation on the constant potential sensor current and the EIS output measurements to generate a sensor output value.

10. The sensor system of claim 9, wherein:
the sensor electrode comprises a glucose sensor electrode; and
the sensor output value comprises a blood glucose value.

11. The sensor system of claim 9, wherein applying the constant voltage potential and performing the EIS procedure occur concurrently.

12. The sensor system of claim 9, wherein the sensor electronics obtains temperature measurement data, wherein the nonlinear mapping operation is performed on the constant potential sensor current, the EIS output measurements, and the temperature measurement data to generate the blood glucose value.

13. The sensor system of claim 9, wherein the nonlinear mapping operation is associated with a sensor characterization model for the glucose sensor.

14. The sensor system of claim 9, wherein the nonlinear mapping operation comprises:
combining the constant potential sensor current and at least some of the EIS output measurements.

15. A sensor system comprising a sensor electrode, one or more processors, and a processor-readable storage medium having executable instructions stored thereon, wherein the executable instructions implement a method comprising:
Obtaining a constant potential sensor current from a glucose sensor, wherein the constant potential current is obtained in response to application of a constant voltage potential to the glucose sensor;
Obtaining electrochemical impedance spectroscopy (EIS) output measurement from the glucose sensor, wherein the EIS output measurements are obtained in response to application of alternating current (AC) voltage signals to the glucose sensor; and
Performing a nonlinear mapping operation on the constant potential sensor current and the EIS output measurement to generate a blood glucose value.

16. The sensor system of claim 15, wherein the nonlinear mapping operation generates the blood glucose value in the absence of any calibration factor for the glucose sensor.

17. The sensor system of claim 15, wherein the method implemented by the executable instructions further comprises:
obtaining temperature measurement data, wherein the nonlinear mapping operation is performed on the constant potential sensor current, the EIS output measurements, and the temperature measurement data to generate the blood glucose value.

18. The sensor system of claim 15, wherein the executable instructions define a sensor characterization model for the glucose sensor.

19. The sensor system of claim 15, wherein the nonlinear mapping operation comprises:
combining the constant potential sensor current and at least some of the EIS output measurements.

20. The sensor system of claim 15, wherein the glucose sensor is integrated with the sensor system.

* * * * *